(12) United States Patent
Inoue et al.

(10) Patent No.: US 6,210,693 B1
(45) Date of Patent: Apr. 3, 2001

(54) OIL-IN-WATER TYPE EMULSIFIED COMPOSITION

(75) Inventors: Haruhiko Inoue; Tohru Okamoto; Hideo Nakajima, all of Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 09/402,466

(22) PCT Filed: Feb. 8, 1999

(86) PCT No.: PCT/JP99/00526

§ 371 Date: Feb. 2, 2000

§ 102(e) Date: Feb. 2, 2000

(87) PCT Pub. No.: WO99/40887

PCT Pub. Date: Aug. 19, 1999

(30) Foreign Application Priority Data

Feb. 10, 1998 (JP) .................................................. 10-044485
Feb. 10, 1998 (JP) .................................................. 10-044486
Jun. 2, 1998 (JP) .................................................. 10-170716

(51) Int. Cl.$^7$ .............................. A61K 31/07; A61K 7/48
(52) U.S. Cl. .......................... 424/401; 424/450; 514/529; 514/938
(58) Field of Search ..................................... 424/401, 450; 514/551, 529, 938

(56) References Cited

U.S. PATENT DOCUMENTS

| | | | | |
|---|---|---|---|---|
| 5,738,858 | * | 4/1998 | Burger | 424/401 |
| 5,744,148 | * | 4/1998 | Habif et al. | 424/401 |
| 5,955,092 | * | 9/1999 | Ranger et al. | 424/401 |
| 5,976,556 | * | 11/1999 | Liu et al. | 424/401 |

FOREIGN PATENT DOCUMENTS 632713  2/1994 (JP) .
8193019  7/1996 (JP) .

* cited by examiner

Primary Examiner—James H. Reamer
(74) Attorney, Agent, or Firm—Townsend & Banta

(57) ABSTRACT

An oil-in-water emulsion composition containing a vitamin A fatty acid ester, which further contains means for preventing oxidation of the vitamin A fatty acid ester and means for preventing hydrolysis of the vitamin A fatty acid ester. The vitamin A fatty acid ester is stabilized in the composition. The composition is particularly suitable for purposes of external-use.

16 Claims, No Drawings

OIL-IN-WATER TYPE EMULSIFIED COMPOSITION

DESCRIPTION

1. Technical Field

The present invention relates to an oil-in-water (O/W) emulsion composition which is primarily used as a composition for external use. More particularly, the present invention relates to an O/W emulsion composition in which a vitamin A fatty acid ester is stabilized.

2. Background Art

Vitamin A and vitamin A fatty acid esters have conventionally been known as effective ingredients for prevention and therapy of keratinization of the skin and retardation of and restoration from aging of the skin. Thus, vitamin A and vitamin A fatty acid esters are incorporated into a variety of external-use compositions formulated for these purposes.

However, vitamin A and vitamin A fatty acid esters are inherently very unstable. That is, they are easily degraded when they undergo isomerization or oxidation evoked by any of a number of factors, such as light, air, heat, and metal ions. Therefore, external-use compositions containing vitamin A or vitamin A fatty acid esters exhibit unsatisfactory stability over time and in addition have drawbacks such as need for particularly careful attention to storage conditions.

Among such unstable vitamin A and vitamin A fatty acid esters, vitamin A has already been a target of a variety of means for stabilization in an external-use composition. Among such means, use of a chelating agent and use of an antioxidant have been proposed.

As compared with vitamin A, fatty acid esters of vitamin A exhibit excellent stability against oxidation, and yet, due to their chemical structure, the fatty acid esters are prone to hydrolysis. Stabilization methods typified by the above methods can improve stability of vitamin A fatty acid esters against oxidation, but cannot improve stability against the problematic hydrolysis.

Accordingly, an object of the present invention is to provide means for enhancing the stability of fatty acid esters of vitamin A against hydrolysis.

DISCLOSURE OF THE INVENTION

In an attempt to attain the above-mentioned objective, the present inventors have carried out extensive studies in search for effective means for stabilizing vitamin A fatty acid esters contained in an O/W emulsion composition, and have found that the objective can be attained by the provision of means for preventing oxidation of vitamin A fatty acid esters together with means for preventing hydrolysis of vitamin A fatty acid esters, thus leading to completion of the present invention.

Accordingly, the present invention provides an O/W emulsion composition containing a vitamin A fatty acid ester, which composition comprises means for preventing oxidation of the vitamin A fatty acid ester together with means for preventing hydrolysis of the vitamin A fatty acid ester.

According to the present invention, the O/W emulsion composition of the present invention can be divided into two cases, depending on the form of the composition: essences and creams.

In the case in which the O/W emulsion composition of the present invention assumes the essence form, the present inventors have found that the aforementioned objective can be attained by incorporating an antioxidant into the oil phase of the composition and also incorporating, as means for preventing hydrolysis of a vitamin A fatty acid ester, a hydrophilic nonionic surfactant or nonionic amphipathic substance under specific conditions.

Thus, the present invention also provides an O/W emulsion composition which assumes, inter alia, an essence form and which comprises means for preventing oxidation of a vitamin A fatty acid ester and means for preventing hydrolysis of the vitamin A fatty acid ester, wherein the means for preventing hydrolysis of the vitamin A fatty acid ester comprises a limited amount of a hydrophilic nonionic surfactant, or, a nonionic amphipathic polymer having a molecular weight of 5,000 or more.

In the case in which the O/W emulsion composition of the present invention assumes the cream form, the present inventors have found that the aforementioned objective can be attained by incorporating an antioxidant into the oil phase of the composition and also incorporating, as means for preventing hydrolysis of a vitamin A fatty acid ester, an amphipathic substance and a hydrophilic nonionic surfactant under specific conditions.

Thus, the present invention also provides an O/W emulsion composition which assumes, inter alia, a cream form and which comprises means for preventing oxidation of a vitamin A fatty acid ester and means for preventing hydrolysis of the vitamin A fatty acid ester, wherein the means for preventing hydrolysis of the vitamin A fatty acid ester comprises an amphipathic substance and a hydrophilic nonionic surfactant, the amphipatic substance and the hydrophilic nonionic surfactant being incorporated into the composition under the following conditions 1) through 3):

1) the gel transition temperature in a three-phase system consisting of the amphipathic substance, the hydrophilic nonionic surfactant, and water is 50° C. or higher;
2) the ratio by weight of the amphipathic substance to the hydrophilic nonionic surfactant is 0.5 or more; and
3) the total amount of all surfactants incorporated into the composition is 5.0% by weight or less with respect to the entirety of the composition.

As used herein, I.O.B. (Inorganic/Organic Balance) value serves as a basis for calculation of Σ I.O.B. value, which is a factor that determines characteristics of the O/W emulsion composition of the present invention, and signifies an index representing the polarity of an oily component. Briefly, I.O.B. represents the ratio of an inorganic value of an oily component to an organic value of the oily component [note: the ratio is calculated as follows: an organic value of 20 is assigned for each carbon atom in the molecule of the oily component, and an inorganic value of 100 is assigned per hydroxyl group in the molecule of the oily component, and these values are used as yardsticks for calculation of an inorganic value of another substituent (inorganic group); see (1) "Organic Analysis" authored by Fujita (1930), published by Kaniya Shoten, (2) "Prediction of Organic Compounds and Organic Conceptional Diagram (Kagaku-no-Ryoiki 11-10)" (1957), pp.719–725, authored by Fujita, (3) "Systematic Organic Qualitative Analysis (Book of Purified Substances)" (1970), p.487, authored by Fujita and Akatsuka, published by Kazama Shoten, (4) "Organic Conceptional Diagram, Its Fundamentals and Applications" (1984), p.227, authored by Koda, published by Sankyo Shuppan, (5) "Design of Emulsion Formulations by use of Organic Conceptional Diagram" (1985), p.98, authored by Yaguchi, published by Nippon Emulsion K. K., and (6) R. H.

Ewell, J. M. Harrison, L. Berg.: Ind. Eng. Chem. 36, 871 (1944)], and is expressed by:

I.O.B.=<inorganic value of the oily component>÷<organic value of the oily component>.

In the present invention, the Σ I.O.B. value is defined as a summation of I.O.B. values of respective oily ingredients which constitute the oil phase of the emulsion.

Thus, Σ I.O.B. is defined as

Σ I.O.B.=<the inorganic value of the oil phase>÷<the organic value of the oil phase>, wherein the inorganic value of the oil phase is expressed by A×x+B×y+C×z+ . . . (wherein A, B, C, . . . represent inorganic values, on an organic conceptional diagram, of the respective oily ingredients which constitute the oil phase of the emulsion and x, y, z, . . . represent proportions of respective oily ingredients A, B, C, . . . which constitute the oil phase of the emulsion, and x+y+z+ . . . =1), and the organic value of the oily phase is expressed by A'×x+B'×y+C'×z+ . . . (wherein A', B', C', . . . represent organic values, on an organic conceptional diagram, of the respective oily ingredients which constitute the oil phase of the emulsion).

The greater the Σ I.O.B. value, the more prominent the inorganic properties of the oil phase, indicating higher polarity.

As will be described hereinbelow, silicone oils are excluded from the category of the aforementioned "respective oily ingredients which constitute the oil phase." Thus, when a silicone oil is present in the oil phase, the silicone oil is ignored for the purpose of calculation of the Σ I.O.B. value.

BEST MODES FOR CARRYING OUT THE INVENTION

Several modes for carrying out the present invention are described below.

As is described above, the O/W emulsion composition of the present invention (hereinafter simply referred to as "the emulsion composition of the present invention") is particularly designed for the stabilization of a vitamin A fatty acid ester incorporated therein.

A. Vitamin A Fatty Acid Ester

As described above, the emulsion composition of the present invention is an O/W emulsion composition containing a vitamin A fatty acid ester.

Examples of the vitamin A fatty acid ester which is contained in the emulsion composition of the present invention and which is to be stabilized include vitamin A acetate, vitamin A palmitate, and vitamin A propionate. No particular limitation is imposed on the type of the ester, so long as it is vitamin A esterified by a fatty acid.

When a mixture of vitamin A fatty acid esters—for example, animal and vegetable oil containing vitamin A fatty acid esters from marine animals or plants—is incorporated into the emulsion composition of the present invention, such vitamin A fatty acid esters contained in the oil are also targets of stabilization according to the present invention.

The emulsion composition of the present invention contains a vitamin A fatty acid ester in an amount of generally not less than 0.0001 wt. % with respect to the entirety of the composition, preferably 0.001–10.0 wt. %, although the amount is not particularly limited.

B. Means for Preventing Oxidation of the Vitamin A Fatty Acid Ester

As is described above, the emulsion composition of the present invention is an O/W emulsion composition comprising means for preventing oxidation of the vitamin A fatty acid ester.

No particular limitation is imposed on the means for preventing oxidation of the vitamin A fatty acid ester, so long as the means can prevent oxidation of the vitamin A fatty acid ester in an O/W emulsion. In the present invention, there may be used antioxidants which are widely used in external-use compositions such as cosmetic compositions. Since the vitamin A fatty acid ester is an oil-phase ingredient in the O/W emulsion, an oil-soluble antioxidant which can act directly on the vitamin A fatty acid ester for the prevention of oxidation in the oil phase is preferably and practically used.

The term "oil-soluble antioxidant" refers to an oil-soluble substance having anti-oxidation capability, and no particular limitation is imposed on the type of the antioxidant, so long as it can be incorporated into an external-use composition in consideration of safety.

Specifically, examples of oil-soluble antioxidants include butylhydroxytoluene (hereinafter referred to as BHT), butylhydroxyanisol (hereinafter referred to as BHA), α-tocopherol, β-tocopherol, γ-tocopherol, δ-tocopherol, nordihydroguaiaretin, propyl gallate, vitamin C fatty acid esters, and sorbic acid. The emulsion composition of the present invention may contain one or more oil-soluble antioxidants.

In order to prevent oxidation of the vitamin A fatty acid ester in the emulsion composition of the present invention, the composition contains preferably an oil-soluble antioxidant in an amount of not less than 0.001 wt. % with respect to the entirety of the composition, more preferably not less than 0.01 wt. %. The maximum amount is not particularly limited, but the composition contains an oil-soluble antioxidant generally in an amount of not more than 10.0 wt. % with respect to the entirety of the composition.

The emulsion composition of the present invention may contain antioxidants other than those described above, including water-soluble antioxidants such as ascorbic acid, in order to prevent oxidation of the below-described ingredients of the composition other than the vitamin A fatty acid ester.

C. Means for Preventing Hydrolysis of the Vitamin A Fatty Acid Ester

The emulsion composition of the present invention is an O/W emulsion composition comprising means for preventing hydrolysis of the vitamin A fatty acid ester as well as the above-described means for preventing oxidation thereof.

The means for preventing hydrolysis of the vitamin A fatty acid ester is selected in accordance with the specific form of the emulsion composition of the present invention. Therefore, the means for preventing hydrolysis depends on the form of the composition; i.e., 1) an essence form or 2) a cream form.

The term "essence form" refers to a viscous solution, and this term is not necessarily drawn to only the limited product form of a "beauty lotion." As used herein, the expression "the emulsion composition of the present invention assumes an essence form" simply means that the emulsion composition of the present invention preferably assumes an essence form, and the composition may be formed into product forms other than beauty lotions, such as lotions, milky lotions, creams, and packs.

In addition, the term "cream form" fundamentally refers to an O/W cream form, in particular, an O/W cream form in which a gel is formed.

1. Means for Preventing Hydrolysis of the Vitamin A Fatty Acid Ester when the Emulsion Composition of the Present Invention is in Essence Form When the emulsion composition of the present invention is in essence form, the following may further be selected as means for preventing hydrolysis of the vitamin A fatty acid ester: (1) incorporation of a hydrophilic nonionic surfactant into the composition in a limited amount (such an emulsion composition is hereinafter referred to as a "first emulsion composition of the present invention"); and (2) incorporation of a nonionic amphipathic polymer having a molecular weight of not less than 5000 into the composition (such an emulsion composition is hereinafter referred to as a "second emulsion composition of the present invention").

(1) Incorporation of a Hydrophilic Nonionic Surfactant into the Composition in a Limited Amount as Means for Preventing Hydrolysis of the Vitamin A Fatty Acid Ester (the first Emulsion Composition of the Present Invention)

As is described above, a hydrophilic nonionic surfactant is incorporated into the first emulsion composition of the present invention in a limited amount as means for preventing primarily hydrolysis of the vitamin A fatty acid ester.

Examples of "hydrophilic nonionic surfactants" which may be incorporated into the first emulsion composition of the present invention include polyoxyethylene (hereinafter referred to as POE) sorbitan fatty acid esters such as POE sorbitan monooleate; POE sorbitol fatty acid esters such as POE sorbitol monooleate; POE glycerin fatty acid esters such as POE glyceryl monostearate and POE glyceryl monoisostearate; POE fatty acid esters such as POE monooleate, POE distearate, and POE dioleate; POE alkyl ethers such as POE oleyl ether, POE stearyl ether, POE behenyl ether, POE 2-octyldodecyl ether, POE 2-hexyldecyl ether, POE 2-heptylundecyl ether, POE 2-decyltetradecyl ether, POE 2-decylpentadecyl ether, and POE cholestanol ether; POE alkylphenyl ethers such as POE octylphenyl ether and POE nonylphenyl ether; pluaronics; POE·polyoxypropylene (hereinafter polyoxypropylene will be referred to as POP) alkyl ethers such as POE·POP cetyl ether and POE·POP 2-decyltetradecyl ether; POE castor oil or hydrogenated castor oil derivatives such as POE castor oil; POE beeswax or lanolin derivatives such as POE sorbitol beeswax; polyglycerin monoalkyl esters or monoalkyl ethers; sucrose fatty acid esters such as sucrose monooleate; and silicone surfactants. The first emulsion composition of the present invention may contain one or more hydrophilic nonionic surfactants.

The lower critical solution temperature of a hydrophilic nonionic surfactant incorporated into the first emulsion composition of the present invention; i.e., a cloud point, is used as an index of hydrophilicity of the surfactant, and the cloud point is preferably not less than 30° C., more preferably not less than 50° C., particularly preferably not less than 70° C.

When a surfactant having a cloud point of less than 30° C. is incorporated into the composition, the surfactant may cause a decrease in stability of the vitamin A fatty acid ester in the composition, which is unsatisfactory.

In view of the foregoing, examples of preferred hydrophilic nonionic surfactants include POE (60) hydrogenated castor oil, POE (40) stearyl ether, and POE (20) oleyl ether, each of which has a cloud point of not less than 70° C.

The ratio by weight of a hydrophilic nonionic surfactant to the oil phase in the first emulsion composition of the present invention is not more than 0.1, preferably not more than 0.05, particularly preferably not more than 0.02.

When the weight ratio of the hydrophilic nonionic surfactant to the oil phase is more than 0.1, the surfactant forms a large number of micelles in the aqueous phase. Consequently, the micelles may cause hydrolysis of the vitamin A fatty acid ester, and the ester may show a strong tendency to exhibit decreased stability, which is unsatisfactory.

When the ratio is less than 0.001, an emulsion condition in the composition becomes unstable, resulting in oil-floating, which is unsatisfactory.

In addition, the total amount of all surfactants incorporated into the first emulsion composition of the present invention including the above-described hydrophilic nonionic surfactant is not more than 1.0 wt. % with respect to the entirety of the composition, preferably not more than 0.5 wt. %. When the total amount of the surfactants is more than 1.0 wt. %, the stability of the vitamin A fatty acid ester may decrease according to composition, which is unsatisfactory.

In addition to the above-described hydrophilic nonionic surfactant, the first emulsion composition of the present invention may contain oleophilic nonionic surfactants, in accordance with needs.

Generally, it is difficult to incorporate other types of surfactants; specifically, cationic surfactants, anionic surfactants, or amphoteric surfactants, into the first emulsion composition of the present invention while maintaining the intended effect of the invention. However, these surfactants may be incorporated into the composition of the present invention.

In the first emulsion composition of the present invention, oily ingredients are preferably selected and incorporated so as to obtain a $\Sigma$ I.O.B. value of the oil phase of not less than 0.043, more preferably not less than 0.128.

When the $\Sigma$ I.O.B. value is less than 0.043, the vitamin A fatty acid ester in the composition may show a tendency to exhibit decreased stability according to composition, which is unsatisfactory.

When the $\Sigma$ I.O.B. value becomes high, polarity of the entire oil phase increases, the vitamin A fatty acid ester hardly transfers into the aqueous phase and to an interface, and the stability of the vitamin A fatty acid ester may improve.

The first emulsion composition of the present invention may contain silicone oil as an oily ingredient. Silicone oil is irrelevant to the $\Sigma$ I.O.B. value, since the oil has fundamentally no carbon atoms in the molecule. When silicone oil is incorporated into the emulsion composition, the oil does not adversely affect the stability of the vitamin A fatty acid ester; i.e., does not impede the intended effect of the present invention, and does not change the $\Sigma$ I.O.B. value.

The first emulsion composition of the present invention preferably contains the above-described oily ingredients in an amount of not less than 1.0 wt. % with respect to the entirety of the composition, more preferably not less than 3.0 wt. %. When the amount is less than 1.0 wt. %, the vitamin A fatty acid ester in the composition shows a strong tendency to exhibit decreased stability, which is unsatisfactory.

Meanwhile, when the total amount of the above-described oily ingredients is in excess of 80.0 wt. %, the composition may not maintain a stable O/W emulsion system, which is unsatisfactory.

No particular limitation is imposed on the oily ingredients incorporated into the first emulsion composition of the present invention, so long as they satisfy the above-described conditions. Specifically, in the first emulsion composition of the present invention, oily ingredients may be appropriately selected from the below-described general examples of those used in external-use compositions so as to satisfy the above-described conditions.

(2) Incorporation of a Nonionic Amphipathic Polymer having a Molecular Weight of not Less than 5000 into the Composition as Means for Preventing Hydrolysis of the Vitamin A Fatty Acid Ester (the second emulsion composition of the present invention)

The expression "a nonionic amphipathic polymer having a molecular weight of not less than 5000" incorporated into the second emulsion composition of the present invention refers to a molecule having nonionic hydrophilic and hydrophobic groups and a molecular weight of not less than 5000. No particular limitation is imposed on the type of polymer, so long as it can be incorporated into an external-use composition in consideration of safety. As is described above, a nonionic amphipathic polymer having a molecular weight of not less than 5000 is incorporated into the second emulsion composition of the present invention as means for primarily preventing hydrolysis of the vitamin A fatty acid ester.

Examples of "nonionic amphipathic polymers having a molecular weight of not less than 5000" which may be incorporated into the second emulsion composition of the present invention include partially-saponified polyvinyl alcohol; cellulose polymers such as methylcellulose, ethylcellulose, methyl hydroxypropyl cellulose, hydroxyethylcellulose, and hydroxypropylcellulose; cellulose derivatives obtained from the modification of the above-described cellulose polymers by use of $C_8$–$C_{30}$ alkyl groups; copolymers of polyvinylpyrrolidone and vinyl compounds having hydrophobic groups; polyether modified silicones such as poly(oxyethylene-oxypropylene) methylpolysiloxane copolymer and dimethylpolysiloxane methy (polyoxyethylene)siloxane copolymer; graft-copolymers of compounds having hydrophobic groups and polyethylene glycol; and alkylated polyoxyethylene. The second emulsion composition of the present invention may contain one or more nonionic amphipathic polymers having a molecular weight of not less than 5000.

The molecular weight of a nonionic amphipatic polymer which is incorporated into the second emulsion composition of the present invention is not less than 5000, preferably not less than 10000, more preferably not less than 20000. When a nonionic amphipatic polymer having a molecular weight of less than 5000 is incorporated into the composition, hydrolysis of the vitamin A fatty acid ester cannot be sufficiently prevented, which is unsatisfactory.

The second emulsion composition of the present invention preferably contains a nonionic amphipathic polymer having a molecular weight of not less than 5000 in an amount of 0.01–10.0 wt. % with respect to the entirety of the composition, more preferably 0.01–3.0 wt. %, particularly preferably 0.01–1.0 wt. %. When the amount is less than 0.01 wt. %, the composition may not be emulsified. When the amount is in excess of 10.0 wt. %, the vitamin A fatty acid ester shows a strong tendency to exhibit decreased stability, and the composition cannot provide satisfaction in use, which is unsatisfactory.

Generally, it is difficult to incorporate general surfactants; specifically, nonionic surfactants, cationic surfactants, anionic surfactants, or amphoteric surfactants into the second emulsion composition of the present invention in addition to a nonionic amphipathic polymer having a molecular weight of not less than 5000, while maintaining the intended effect of the invention, since incorporation of general surfactants possibly impedes the intended effect. However, these general surfactants may be incorporated into the composition of the present invention.

In the second emulsion composition of the present invention, one or more oily ingredients are preferably selected and incorporated so as to obtain a Σ I.O.B. value of the oil phase of not less than 0.043, more preferably not less than 0.128. When the Σ I.O.B. value is less than 0.043, the vitamin A fatty acid ester in the composition may show a tendency to exhibit decreased stability according to composition, which is unsatisfactory.

When the Σ I.O.B. value becomes high, polarity of the entire oil phase increases, and the vitamin A fatty acid ester hardly transfers into the aqueous phase and to an interface, and the stability of the vitamin A fatty acid ester can be enhanced.

The second emulsion composition of the present invention may contain silicone oil as an oily ingredient. Silicone oil is irrelevant to the Σ I.O.B. value, since the oil has fundamentally no carbon atoms in its molecule. When silicone oil is incorporated into the emulsion composition, the oil does not adversely affect the stability of a vitamin A fatty acid ester; i.e., the intended effect of the present invention, and does not change the Σ I.O.B. value.

The second emulsion composition of the present invention preferably contains the above-described oily ingredients in an amount of not less than 1.0 wt. % with respect to the entirety of the composition, more preferably not less than 3.0 wt. %. When the amount is less than 1.0 wt. %, the vitamin A fatty acid ester in the composition shows a strong tendency to exhibit decreased stability, which is unsatisfactory.

Meanwhile, when the amount of the above-described oily ingredients is in excess of 80.0 wt. %, the composition may not maintain a stable O/W emulsion system, which is unsatisfactory.

No particular limitation is imposed on the oily ingredients incorporated into the second emulsion composition of the present invention, so long as they satisfy the above-described conditions. Specifically, in the second emulsion composition of the present invention, oily ingredients may be appropriately selected from the below-described general examples of those used in external-use compositions so as to satisfy the above-described conditions.

2. Means for Preventing Hydrolysis of the Vitamin A Fatty Acid Ester when the Emulsion Composition of the Present Invention is in a Cream Form The emulsion composition of the present invention of the present mode (hereinafter referred to as "the third emulsion composition of the present invention") is an O/W emulsion composition different from the first or second emulsion composition of the present invention. The composition of the present mode in which a gel is formed to prevent hydrolysis of the vitamin A fatty acid ester.

In the third emulsion composition of the present invention, means for preventing hydrolysis of the vitamin A fatty acid ester comprises incorporation of an amphipathic substance and a hydrophilic nonionic surfactant under particular conditions.

An amphipathic substance which may be incorporated into the third emulsion composition of the present invention is a substance having high hydrophobicity and low surface activity as compared with a general surfactant. No particular limitation is imposed on the amphipathic substance, so long as it has the above-described properties, and, for example, a higher aliphatic alcohol, monoglyceride, or glyceryl monoalkyl ether may be used. The third emulsion composition of the present invention may contain one or more amphipathic substances.

Examples of "hydrophilic nonionic surfactants" which may be incorporated into the third emulsion composition of the present invention include POE sorbitan fatty acid esters such as POE sorbitan monooleate; POE sorbitol fatty acid esters such as POE sorbitol monooleate; POE glycerin fatty acid esters such as POE glyceryl monostearate and POE glyceryl monoisostearate; POE fatty acid esters such as POE monooleate, POE distearate, and POE dioleate; POE alkyl ethers such as POE oleyl ether, POE stearyl ether, POE behenyl ether, POE 2-octyldodecyl ether, POE 2-hexyldecyl ether, POE 2-heptylundecyl ether, POE 2-decyltetradecyl ether, POE 2-decylpentadecyl ether, and POE cholestanol ether; POE alkylphenyl ethers such as POE octylphenyl ether and POE nonylphenyl ether; pluaronics; POE·POP alkyl ethers such as POE-POP cetyl ether and POE·POP 2-decyltetradecyl ether; POE castor oil or hydrogenated castor oil derivatives such as POE castor oil; POE beeswax or lanolin derivatives such as POE sorbitol beeswax; polyglycerin monoalkyl esters or monoalkyl ethers; sucrose fatty acid esters such as sucrose monooleate; and silicone surfactants. The third emulsion composition of the present invention may contain one or more hydrophilic nonionic surfactants.

In the third emulsion composition of the present invention, the above-described amphipathic substance and hydrophilic nonionic surfactant form a gel in an amphipathic substance-hydrophilic nonionic surfactant-water system. The system should have an appropriate combination of these substances so as to provide a gel transition temperature of not less than 50° C., preferably not less than 60° C.

When the gel transition temperature is less than 50° C., the vitamin A fatty acid ester in the composition exhibits decreased stability, which is unsatisfactory.

The weight ratio of the amphipathic substance to the hydrophilic nonionic surfactant should be not less than 0.5, preferably not less than 0.7, more preferably not less than 1.0.

When the ratio is less than 0.5, the vitamin A fatty acid ester in the composition exhibits decreased stability, which is unsatisfactory.

In addition, the total amount of surfactants which are incorporated into the third emulsion composition of the present invention including the above-described hydrophilic nonionic surfactant should be not more than 5.0 wt. % with respect to the entirety of the composition, preferably not more than 3.0 wt. %.

When the amount of the surfactants is more than 5.0 wt. %, the vitamin A fatty acid in the composition exhibits decreased stability, which is unsatisfactory.

In accordance with needs, the third emulsion composition of the present invention may contain an oleophilic nonionic surfactant in addition to the above-described hydrophilic nonionic surfactant.

Generally, it is difficult to incorporate other types of surfactants; specifically, cationic surfactants, anionic surfactants, or amphoteric surfactants into the third emulsion composition of the present invention while maintaining the intended effect of the invention. However, these surfactants may be incorporated into the present invention.

In the third emulsion composition of the present invention, oily ingredients are preferably selected and incorporated so as to obtain a $\Sigma$ I.O.B. value of the oil phase of not less than 0.043, more preferably not less than 0.128.

When the $\Sigma$ I.O.B. value is less than 0.043, the vitamin A fatty acid ester in the composition may show a tendency to exhibit decreased stability according to composition, which is unsatisfactory.

When the $\Sigma$ I.O.B. value becomes high, polarity of the entire oil phase increases, the vitamin A fatty acid ester hardly transfers into the aqueous phase, and the stability of the vitamin A fatty acid ester in the oil phase may improve.

The third emulsion composition of the present invention may contain silicone oil as an oily ingredient. Silicone oil is irrelevant to the $\Sigma$ I.O.B. value, since the oil has fundamentally no carbon atoms in its molecule. When silicone oil is incorporated into the emulsion composition, the oil does not adversely affect the stability of the vitamin A fatty acid ester; i.e., the intended effect of the present invention, and does not change the $\Sigma$ I.O.B. value.

The third emulsion composition of the present invention preferably contains the above-described oily ingredients in an amount of not less than 1.0 wt. % with respect to the total amount of the above-described amphipathic substance and hydrophilic nonionic surfactant, more preferably not less than 2.0 wt. %.

When the amount is less than 1.0 wt. %, the vitamin A fatty acid ester in the composition shows a tendency to exhibit decreased stability, which is unsatisfactory.

In the third emulsion composition of the present invention, even when a relatively large amount of a hydrophilic nonionic surfactant is incorporated, the surfactant coexist with an amphipathic substance to form a gel, resulting in reduction or elimination of the free surfactant. The present inventors have considered that the above phenomenon can be used as means for drastically enhancing the stability of the vitamin A fatty acid ester in the composition. The third emulsion composition of the present invention has been accomplished based on this consideration.

No particular limitation is imposed on oily ingredients incorporated in the third emulsion composition of the present invention, so long as they satisfy the above-described conditions. Specifically, in the third emulsion composition of the present invention, oily ingredients may be appropriately selected from the below-described general examples of those used in external-use compositions so as to satisfy the above-described conditions.

D. External-Use Composition of the Present Invention

In any of its modes, the emulsion composition of the present invention is an O/W emulsion composition which may be used primarily as an external-use composition such as a cosmetic composition, a drug, or a quasi-drug. When the emulsion composition of the present invention is used as an external-use composition, it will be referred to as "the external-use composition of the present invention." The external-use composition may be represented as a first, second, or third external-use composition of the present invention corresponding to the respective modes of the present invention described above. Unless otherwise stated, the expression "external-use composition of the present invention" refers to all of the three modes.

The external-use composition of the present invention is described in detail hereinbelow.

In accordance with the specific purpose, the external-use composition of the present invention may contain pharmaceutically active ingredients or base ingredients, so long as they do not impede the intended effect of the present invention; i.e., stabilization of the vitamin A fatty acid ester in the composition.

For example, when the external-use composition of the present invention is used as a sun-care product, the composition may contain the following pharmaceutically active ingredients: benzoic acid ultraviolet absorbers such as p-aminobenzoic acid; anthranilic acid ultraviolet absorbers such as methyl anthranilate; salicylic acid ultraviolet absorbers such as octyl salicylate, phenyl salicylate, and homomenthyl salicylate; cinnamic acid ultraviolet absorbers such as isopropyl p-methoxycinnamate, octyl p-methoxycinnamate, 2-ethylhexyl p-methoxycinnamate, glyceryl octanoate di-p-methoxycinnamate, and [4-bis(trimethylsiloxy)methylsilyl-3-methylbutyl]-3,4,5-trimethoxycinnamic acid ester; benzophenone ultraviolet absorbers such as 2,4-dihydroxybenzophenone, 2-hydroxy-4-methoxybenzophenone, 2-hydroxy-4-methoxybenzophenone-5-sulfonic acid, sodium 2-hydroxy-4-methoxybenzophenone-5-sulfonate; and ultraviolet absorbers such as urocanic acid, ethyl urocanate, 2-phenyl-5-methylbenzoxazole, 2-(2'-hydroxy-5'-methylphenyl)benzotriazole, and 4-t-butyl-4'-methoxydibenzoylmethane.

In order to obtain a humectant effect, the external-use composition of the present invention may contain the following humectants: polyethylene glycol, propylene glycol, dipropylene glycol, 1,3-butylene glycol, hexylene glycol, glycerol, diglycerin, xylitol, maltitol, maltose, D-mannitol, starch syrup, glucose, fructose, lactose, sodium chondroitin sulfate, sodium hyaluronate, sodium adenosine phosphate, sodium lactate, bile salts, pyrrolidonecarboxylic acid, glucosamine, and cyclodextrin.

Furthermore, the external-use composition may contain as pharmaceutically active ingredients vitamins which can be used for purposes other than antioxidants; hormones such as estradiol and ethynylestradiol; amino acids such as arginine, aspartic acid, cystine, cysteine, methionine, serine, leucine, and tryptophan; anti-inflammation agents such as allantoin, azulene, and glycyrrhetinic acid; whitening agents such as arbutin; astringents such as zinc oxide and tannic acid; refrigerants such as L-menthol and camphor; sulfur; lysozyme chloride; pyridoxine hydrochloride; and γ-oryzanol.

Furthermore, the external-use composition of the present invention may contain extracts having a variety of pharmaceutical activity, such as houttuynia extract, phellodendron bark extract, sweet clover extract, hypericum extract, glycyrrhiza extract, paeony root extract, saponaria extract, sponge gourd extract, cinchona extract, saxifrage extract, sophora root extract, nuphar extract, fennel extract, Primula Veris extract, Primula vulgaris extract, rose extract, rehmannia root extract, lemon extract, lithospermum root extract, aloe extract, calamus rhizome extract, eucalyptus extract, horsetail extract, sage extract, thyme extract, green tea extract, seaweed extract, cucumber extract, clove extract, raspberry extract, balm mint extract, ginseng exract, horse chestnut extract, peach extract, peach leaf extract, mulberry bark extract, cornflower extract, witch hazel extract, placenta extract, thymus extract, and silk extract.

Pharmaceutically active ingredients which can be incorporated into the external-use composition of the present invention are not limited to the above-described pharmaceutically active ingredients. In addition, in accordance with needs, the above-described ingredients may be incorporated into the external-use composition singly or in combination of two or more.

In accordance with the specifically desired form and product form, generally known base ingredients may be incorporated into the external-use composition, so long as they do not impede the intended effect of the present invention. Particularly, oily ingredients should be carefully incorporated.

Accordingly, the external-use composition of the present invention may contain liquid fats and oils such as linseed oil, camellia oil, macadamia nut oil, corn oil, mink oil, olive oil, avocado oil, sasanqua oil, castor oil, safflower oil, apricot kernel oil, cinnamon oil, jojoba oil, grape seed oil, sunflower oil, almond oil, rape seed oil, sesame oil, wheat germ oil, rice germ oil, rice bran oil, cotton seed oil, soybean oil, peanut oil, tea seed oil, evening primrose oil, egg yolk oil, beef foot oil, cod liver oil, triglycerin, glyceryl trioctanoate, and glyceryl triisopalmitate; liquid or solid fats and oils such as coconut oil, palm oil, and palm kernel oil; solid fats and oils such as cacao butter, beef tallow, mutton tallow, lard, horse fat, hydrogenated oil, hydrogenated castor oil, Japan wax, and shea butter; and waxes such as beeswax, candelilla wax, cotton wax, carnauba wax, bayberry wax, insect wax, spermaceti, montan wax, rice bran wax, lanolin, hydrogenated lanolin, hard lanolin, kapok wax, sugar cane wax, jojoba wax, and shellac wax.

Furthermore, the external-use composition of the present invention may contain ester oils, including octanoic acid esters such as cetyl octanoate, isooctanoic acid esters such as glyceryl tri-2-ethylhexanoate and pentaerythritol tetra-2-ethylhexanoate, lauric acid esters such as hexyl laurate, myristic acid esters such as isopropyl myristate and octyl-dodecyl myristate, palmitic acid esters such as octy palmitate, stearic acid esters such as isocetyl stearate, isostearic acid esters such as isopropyl isostearate, isopalmitic esters such as octyl isopalmitate, oleic acid esters such as isodecyl oleate, adipic acid diesters such as diisopropyl adipate, sebacic acid diesters such as diethyl sebacate, and diisostearyl malate; and hydrocarbon oils such as liquid paraffin, ozokerite, squalane, squalene, pristane (2,6,10,14-tetramethylpentadecane), paraffin, isoparaffin, ceresine, vaseline (petrolatum), microcrystalline wax.

Furthermore, the external-use composition of the present invention may contain silicones having a linear structure, such as dimethyl polysiloxane, methylphenyl polysiloxane, and methyl hydrogen polysiloxane; cyclic silicones such as octamethylcyclotetrasiloxane, decamethylcyclopentasiloxane, and dodecamethylcyclohexasiloxane; silicone resins having a three-dimensional network structure; and silicones such as silicone rubber.

Furthermore, the external-use composition may contain lower alcohols such as methanol, ethanol, propanol, and isopropanol; and sterols such as cholesterol, sitosterol, phytosterol, and lanosterol.

Furthermore, the external-use composition of the present invention may contain plant polymers such as gum arabic, tragacanth gum, galactan, carob gum, guar gum, karaya gum, carrageenan, pectin, agar, quince seed (Cydonia vulgaris Pers (Rosaceae)), algae colloid (seaweed extract), and starches (rice, corn, potato, or wheat); microorganism polymers such as dextran, succinoglucan, and pullulan; starch polymers such as carboxymethyl starch and methylhydroxypropyl starch; animal polymers such as collagen, casein, albumin, and gelatin; cellulose polymers such as methylcellulose, nitrocellulose, ethylcellulose, hydroxypropyl methylcellulose, hydroxyethylcellulose, sodium cellulose sulfate, hydroxypropylcellulose, sodium carboxymethyl cellulose, crystalline cellulose, and cellulose powder; alginate polymers such as sodium alginate and propyleneglycol alginate; vinyl polymers such as polyvinyl methyl ether and carboxyvinylpolymer (e.g. CARBOPOL); polyoxyethylene polymers; polyoxyethylene polyoxypropylene copolymers; acrylic polymers such as sodium polyacrylate, poly(ethyl acrylate), and polyacrylamide; and water-soluble polymers including inorganic water-soluble polymers such as polyethyleneimine, cation polymers, bentonite, magnesium aluminum silicate, laponite, hectorite, and silicic anhydride.

The external-use composition of the present invention may also contain sequestering agents such as alanine, sodium edetate, sodium polyphosphate, sodium metaphosphate, and phosphoric acid; and pH adjusting agents such as 2-amino-2-methyl-1-propanol, 2-amino-2-methyl-1,3-propanediol, potassium hydroxide, sodium hydroxide, L-arginine, L-lysine, triethanolamine, sodium carbonate, lactic acid, citric acid, glycollic acid, succinic acid, tartaric acid, DL-malic acid, potassium carbonate, sodium bicarbonate, and ammonium bicarbonate.

The external-use composition of the present invention may also contain antimicrobial agents such as benzoic acid, salicylic acid, phenol, parahydroxybenzoic acid esters or parabens, p-chloro-m-cresol, hexachlorophene, benzalkonium chloride, chlorohexdin hydrochloride, trichlorocarbanilide, photosensitive dyes, and 2-phenoxyethanol.

In accordance with needs, the external-use composition of the present invention may also contain appropriate perfumes or coloring agents, so long as they do not impede the intended effect of the present invention.

Base ingredients which may be incorporated into the external-use composition of the present invention are not limited to the above-described base ingredients.

In accordance with formulation of the desired product form, the base ingredients may be incorporated into the external-use composition in appropriate combination.

Specific formulations of the external-use composition of the present invention are described below.

EXAMPLES

The present invention will next be described in more detail by way of examples, which should not be construed as limiting the invention thereto.

Throughout the examples, unless otherwise stated, the amount of an incorporated ingredient represents weight % with respect to the entirety of the product containing the ingredient.

Method for Evaluating the Stability of a Vitamin A Fatty Acid Ester

In the Examples, the percent residue of the vitamin A fatty acid ester in the product is used as an index for evaluating the stability of the ester incorporated into the product. The percent residue of the ester in the product was obtained as follows: the product containing the ester was covered with aluminum foil for protection against light and stored at 50° C. for one month, and subsequently, the product was analyzed by high performance liquid chromatography, and then the amount of the remaining ester was compared with the amount of ester in the product before storage to thereby calculate the percent residue of the ester (%). (The thus-obtained percent residue of the ester is hereinafter referred to as "percent residue.").

In order to obtain percent residue, high performance liquid chromatography was performed under the following conditions.

Column: C18 column (product of Shiseido Co., Ltd.)
Detection: UV 310 nm.
Mobile phase: 72% methanol/10% acetonitrile/18% ion-exchange water/0.5% acetic acid (in the case of detection of retinol acetate); 100% methanol/0.5% acetic acid (in the case of detection of retinol palmitate)

The percent residue is preferably close to 100%, and in the present invention, a percent residue of 80% is regarded as a benchmark value for evaluating the stabilization of the vitamin A fatty acid ester in the product.

Therefore, when the percent residue is not less than 80%, the product is considered satisfactory, whereas when it is less than 80%, the product is considered unsatisfactory.

Method for Calculating the Σ I.O.B. Value

The Σ I.O.B. value of the oil phase in the product of each example was calculated based on the above-described method.

A. The First Emulsion Composition of the Present Invention or the First External-Use Composition of the Present Invention The products of the examples and the comparative examples shown in the following Tables A1 and A2 were subjected to the above-described analysis and calculation in order to evaluate the effect of the present invention. The results are shown in the tables.

In order to prepare the respective products in the tables, the oil phase components, which were maintained at 70° C., were added to the aqueous phase components, which were maintained at room temperature, and the resultant mixture was emulsified homogeneously by use of a homogenization mixer and cooled to room temperature.

TABLE A1

|  | Example | | | | | | | | Comparative Example | | |
| --- | --- | --- | --- | --- | --- | --- | --- | --- | --- | --- | --- |
|  | A1 | A2 | A3 | A4 | A5 | A6 | A7 | A8 | A1 | A2 | A3 |
| (Oil phase) | | | | | | | | | | | |
| Retinol acetate | 0.2 | 0.2 | 0.2 | 0.2 | 0.2 | 0.2 | 0.2 | 0.2 | 0.2 | 0.2 | 0.2 |
| BHT | 0.1 | 0.1 | 0.1 | 0.1 | 0.1 | 0.1 | 0.1 | 0.1 | 0.1 | 0.1 | — |
| Pentaerythritol tetra-2-ethyl-hexanoate | 10.0 | 10.0 | 10.0 | 10.0 | 5.0 | 3.0 | 1.0 | 0.7 | 10.0 | 30.0 | 10.0 |
| POE (20) stearyl ether | 1.0 | 0.5 | 0.2 | 0.1 | 0.01 | 0.01 | 0.01 | 0.01 | 2.0 | 2.0 | 0.1 |
| (Aqueous phase) | | | | | | | | | | | |
| Trisodium edetate | 0.02 | 0.02 | 0.02 | 0.02 | 0.02 | 0.02 | 0.02 | 0.02 | 0.02 | 0.02 | 0.02 |
| Carboxyvinylpolymer | 0.3 | 0.3 | 0.3 | 0.3 | 0.3 | 0.3 | 0.3 | 0.3 | 0.3 | 0.3 | 0.3 |
| KOH | 0.1 | 0.1 | 0.1 | 0.1 | 0.1 | 0.1 | 0.1 | 0.1 | 0.1 | 0.1 | 0.1 |
| Glycerin | 5.0 | 5.0 | 5.0 | 5.0 | 5.0 | 5.0 | 5.0 | 5.0 | 5.0 | 5.0 | 5.0 |
| Methylparaben | 0.1 | 0.1 | 0.1 | 0.1 | 0.1 | 0.1 | 0.1 | 0.1 | 0.1 | 0.1 | 0.1 |
| Ion-exchange water | B | B | B | B | B | B | B | B | B | B | B |
| Σ I.O.B. Estimation | 0.353 | 0.353 | 0.353 | 0.353 | 0.353 | 0.353 | 0.353 | 0.353 | 0.353 | 0.353 | 0.353 |
| Percent residue of retinol acetate (%) (50° C., one month) | 82 | 84 | 86 | 87 | 86 | 83 | 82 | 81 | 73 | 75 | 68 |

*B: Balance

The products of Examples A1 through A4 shown in Table A1 were compared in terms of stability of retinol acetate serving as the vitamin A fatty acid ester, in accordance with the amount of POE (20) stearyl ether serving as a hydrophilic nonionic surfactant which is incorporated within the allowable range. As is apparent from Table A1, when the surfactant content is low, the vitamin A fatty acid ester exhibits slightly improved stability over time.

The products of Examples A5 through A7 were compared in terms of stability of the vitamin A fatty acid ester in accordance with the amount of pentaerythritol tetra-2-ethylhexanoate which is incorporated as an oily ingredient within the allowable range, while a small amount of POE (20) stearyl ether serving as a hydrophilic nonionic surfactant was incorporated within the allowable range. (In this case, the surfactant exhibits a minimum effect on the stability of the vitamin A fatty acid ester.) As is apparent from Table A1, in the product of Example A7, wherein the minimum amount of the oily ingredient is incorporated within the preferred range, the stability of the vitamin A fatty acid ester is close to the allowable limit.

As is also apparent from Table A1, in the product of Example A8, wherein the amount of the oily ingredient is within the allowable range but outside the preferred range, the stability of the vitamin A fatty acid ester is closer to the allowable limit than in the cases of the products of Examples A5 through A7.

As compared with the above-described Examples, in the products of Comparative Examples 1 and 2, the amount of the incorporated hydrophilic nonionic surfactant is outside the allowable range, and in the product of Comparative Example 3, BHT serving as an oil-soluble antioxidant is not incorporated. As is apparent from Table A1, in all products of the Comparative Examples, the stability of the vitamin A fatty acid ester over time is poor; i.e., the percent residue is less than the benchmark value, 80%.

As is apparent from the above results, the first emulsion composition of the present invention containing ingredients within the allowable range exhibits the intended effect, whereas the composition containing ingredients outside the allowable range does not exhibit the intended effect.

TABLE A2

| | Example | | | |
|---|---|---|---|---|
| | A9 | A10 | A11 | A12 |
| (Oil phase) | | | | |
| Retinol acetate | 0.2 | 0.2 | 0.2 | 0.2 |
| BHT | 0.05 | 0.05 | 0.05 | 0.05 |
| Squalane | 20.0 | 20.0 | 20.0 | 20.0 |
| POE (20) oleyl ether | 0.3 | — | — | — |
| POE (10) oleyl ether | — | 0.3 | — | — |
| POE (7) oleyl ether | — | — | 0.3 | — |
| POE (5) oleyl ether | — | — | — | 0.3 |
| (Aqueous phase) | | | | |
| Trisodium edetate | 0.02 | 0.02 | 0.02 | 0.02 |
| Carboxyvinylpolymer | 0.3 | 0.3 | 0.3 | 0.3 |
| KOH | 0.08 | 0.08 | 0.08 | 0.08 |
| Glycerin | 5.0 | 5.0 | 5.0 | 5.0 |
| Methylparaben | 0.2 | 0.2 | 0.2 | 0.2 |
| Ion-exchange water | Balance | Balance | Balance | Balance |
| Cloud point | 90° C. | 60° C. | 30° C. | 25° C. |
| Σ I.O.B. | 0 | 0 | 0 | 0 |
| Estimation | | | | |
| Percent residue of retinol acetate (%) (50° C., one month) | 90 | 89 | 85 | 81 |

The products of Examples A9 through A12 shown in Table A2 were compared in terms of stability of the vitamin A fatty acid ester, in accordance with the cloud point of an incorporated hydrophilic nonionic surfactant. As is apparent from Table A2, the vitamin A fatty acid ester exhibits improved stability over time when a hydrophilic nonionic surfactant having a high cloud point is incorporated.

As is also apparent from Table A2, in the product of Example A12 which contains a hydrophilic nonionic surfactant having a cloud point within the allowable range but outside the preferred range, the stability of the vitamin A fatty acid ester is close to the allowable limit; i.e., the percent residue is close to the benchmark value.

TABLE A3

| | Example | | | | | | |
|---|---|---|---|---|---|---|---|
| | A13 | A14 | A15 | A16 | A17 | A18 | A19 |
| (Oil phase) | | | | | | | |
| Retinol acetate | 0.2 | 0.2 | 0.2 | 0.2 | 0.2 | 0.2 | 0.2 |
| BHT | 0.05 | 0.05 | 0.05 | 0.05 | 0.05 | 0.05 | 0.05 |
| Pentaerythritol tetra-2-ethyl-hexanoate | — | 5.0 | 10.0 | 15.0 | 20.0 | — | 20.0 |
| squalane | 20.0 | 15.0 | 10.0 | 5.0 | — | — | — |
| Cetyl 2-ethylhexanoate | — | — | — | — | — | 20.0 | — |
| Glyceryl tri-2-ethylhexanoate | — | — | — | — | — | — | 20.0 |
| POE (60) hydrogenated castor oil | 0.7 | 0.7 | 0.7 | 0.7 | 0.7 | 0.7 | 0.7 |
| (Aqueous phase) | | | | | | | |
| Trisodium edetate | 0.02 | 0.02 | 0.02 | 0.02 | 0.02 | 0.02 | 0.02 |
| Carboxyvinylpolymer | 0.3 | 0.3 | 0.3 | 0.3 | 0.3 | 0.3 | 0.3 |
| KOH | 0.08 | 0.08 | 0.08 | 0.08 | 0.08 | 0.08 | 0.08 |
| Glycerin | 5.0 | 5.0 | 5.0 | 5.0 | 5.0 | 5.0 | 5.0 |
| Methylparaben | 0.2 | 0.2 | 0.2 | 0.2 | 0.2 | 0.2 | 0.2 |

TABLE A3-continued

|  | Example | | | | | | |
|---|---|---|---|---|---|---|---|
|  | A13 | A14 | A15 | A16 | A17 | A18 | A19 |
| Ion-exchange water | B | B | B | B | B | B | B |
| Σ I.O.B. Estimation | 0 | 0.088 | 0.177 | 0.265 | 0.353 | 0.128 | 0.353 |
| Percent residue of retinol acetate (%) (50° C., one month) | 81 | 84 | 88 | 92 | 94 | 85 | 93 |

B: Balance

The products of Examples A13 through A19 shown in Table A3 were studied in terms of correlation between stability of the vitamin A fatty acid ester over time and Σ I.O.B value, in accordance with composition of ingredients in the oil phase.

As is apparent from Table A3, when the Σ I.O.B value is high; i.e., when the oil phase of the composition has high inorganic properties and polarity, the vitamin A fatty acid ester exhibits improved stability over time.

TABLE A4

|  | Example A20 | Example A21 | Comparative Example A4 |
|---|---|---|---|
| (Oil phase) | | | |
| Retinol palmitate | 0.2 | 0.2 | 0.2 |
| BHT | 0.1 | 0.1 | 0.1 |
| Pentaerythritol tetra-2-ethylhexanoate | 20.0 | — | 0.8 |
| Di (2-ethylhexyl) succinate | — | 20.0 | — |
| POE (20) behenyl ether | 0.2 | — | 0.2 |
| Polyoxyethylene (25) polyoxypropylene glycol (30) | — | 0.5 | — |
| (Aqueous phase) | | | |
| Trisodium edetate | 0.02 | 0.02 | 0.02 |
| Carboxyvinylpolymer | 0.3 | 0.3 | 0.3 |
| KOH | 0.1 | 0.1 | 0.1 |
| Glycerin | 5.0 | 5.0 | 5.0 |
| Methylparaben | 0.1 | 0.1 | 0.1 |
| Ion-exchange water | Balance | Balance | Balance |
| Σ I.O.B. Estimation | 0.353 | 0.316 | 0.353 |
| Percent residue of retinol palmitate (%) (50° C., one month) | 90 | 88 | 35 |

In the products of Examples A20 and A21 and Comparative Example A4 shown in Table A4, retinol palmitate is used as a vitamin A fatty acid ester.

As is apparent from Table A4, in the products of Examples wherein all incorporated ingredients fall within the allowable ranges, the vitamin A fatty acid exhibits improved stability over time, whereas in the product of Comparative Example A4, wherein the weight ratio of POE (20) behenyl ether serving as a hydrophilic nonionic surfactant to pentaerythritol tetra-2-ethylhexanoate serving as an oily ingredient is 0.25, which is outside the allowable range (i.e. 0.1), the stability of the vitamin A fatty acid ester decreases considerably.

In the first emulsion composition of the present invention, whichever vitamin A fatty acid ester is incorporated, the ester improves in terms of stability over time.

In addition, as typical modes of the first emulsion composition or the first external-use composition of the present invention, a beauty lotion (Example A22) and a milky lotion (Example A23) of the following formulations were prepared in accordance with conventional methods. The beauty lotion and the milky lotion were subjected to the above-described analysis, to thereby obtain the percent residue of retinol acetate, which was not less than 80%. Therefore, the result showed that the first emulsion composition or the first external-use composition of the present invention is very excellent in terms of stability of retinol acetate over time.

| ingredient | amount (wt. %) |
|---|---|
| (Example A22) Beauty lotion | |
| (oil phase) | |
| retinol acetate | 0.2 |
| BHT | 0.1 |
| glyceryl tri-2-ethylhexanoate | 5.0 |
| cetyl 2-ethylhexanoate | 5.0 |
| liquid paraffin | 5.0 |
| POE (20) behenyl ether | 0.2 |
| (aqueous phase) | |
| trisodium edetate | 0.02 |
| carboxyvinylpolymer | 0.3 |
| KOH | 0.1 |
| glycerin | 10.0 |
| methylparaben | 0.2 |
| ion-exchange water | balance |
| (Example A23) Milky lotion | |
| (oil phase) | |
| retinol acetate | 0.2 |
| BHT | 0.1 |
| pentaerythritol tetra-2-ethylhexanoate | 10.0 |
| di (2-ethylhexyl) succinate | 10.0 |
| POE (20) behenyl ether | 0.2 |
| behenyl alcohol | 0.2 |
| stearyl alcohol | 0.1 |
| ethylparaben | 0.1 |
| butylparaben | 0.1 |
| (aqueous phase) | |
| trisodium edetate | 0.02 |
| carboxyvinylpolymer | 0.2 |
| KOH | 0.05 |
| glycerin | 10.0 |
| ion-exchange water | balance |

B. The Second Emulsion Composition of the Present Invention or the Second External-Use Composition of the Present Invention The products of the Examples and the Comparative Examples shown in the following Tables B1 and B2 were subjected to the above-described analysis and calculation, in order to evaluate the effect of the present invention. The results are shown in the tables.

In order to prepare each product in the tables, the oil phase components, which were maintained at 70° C., were added to the aqueous phase components, which were maintained at room temperature, and the resultant mixture was emulsified homogeneously by use of a homogenization mixer and cooled to room temperature.

TABLE B1

|  | Example | | | Comparative Example | |
|---|---|---|---|---|---|
|  | B1 | B2 | B3 | B1 | B2 |
| (Oil phase) | | | | | |
| Retinol acetate | 0.2 | 0.2 | 0.2 | 0.2 | 0.2 |
| BHT | 0.1 | 0.1 | 0.1 | 0.1 | — |
| Pentaerythritol tetra-2-ethyl-hexanoate | 20.0 | 20.0 | 10.0 | 20.0 | 20.0 |
| PVA EG-05 | 5.0 | — | — | — | — |
| NATROSOL Plus330 | — | 3.0 | — | — | — |
| Poly(oxyethylene · oxypropylene) methylpolysiloxane copolymer | — | — | 1.0 | — | — |
| POE (20) stearyl ether | — | — | — | 5.0 | — |
| POE (60) hydrogenated castor oil | — | — | — | — | 5.0 |
| (Aqueous phase) | | | | | |
| Trisodium edetate | 0.02 | 0.02 | 0.02 | 0.02 | 0.02 |
| Carboxyvinyl-polymer | 0.3 | 0.3 | 0.3 | 0.3 | 0.3 |
| KOH | 0.1 | 0.1 | 0.1 | 0.1 | 0.1 |
| Glycerin | 5.0 | 5.0 | 5.0 | 5.0 | 5.0 |

TABLE B1-continued

|  | Example | | | Comparative Example | |
|---|---|---|---|---|---|
|  | B1 | B2 | B3 | B1 | B2 |
| Methylparaben | 0.1 | 0.1 | 0.1 | 0.1 | 0.1 |
| Ion-exchange water | Balance | Balance | Balance | Balance | Balance |
| Σ I.O.B. value | 0.353 | 0.353 | 0.353 | 0.353 | 0.353 |
| Percent residue of retinol acetate (%) | 92 | 95 | 91 | 58 | 52 |
| Estimation | Passed | Passed | Passed | Not passed | Not passed |

In the products of Examples B1 through B3 shown in Table B1, within the allowable range, there is incorporated, as a nonionic amphipathic polymer having a molecular weight of not less than 5000, PVA EG-05 (product of The Nippon Synthetic Chemical Industry Co., Ltd., MW: 30,000), NATROSOL Plus330 (product of Hercules, MW: 1,500,000), or poly(oxyethylene.oxypropylene) methylpolysiloxane copolymer (MW: 50,000). In contrast, in the product of Comparative Example B1, polyoxyethylene (referred to as POE in the table) (20) stearyl ether serving as a nonionic surfactant is incorporated in lieu of the nonionic amphipathic polymer, and in the product of Comparative Example B2, polyoxyethylene (referred to as POE in the table) (60) hydrogenated castor oil serving as a nonionic surfactant is incorporated, but BHT serving as an oil-soluble antioxidant is not incorporated.

As is apparent from Table B1, the products of Examples B1 through B3, each of which contains a nonionic amphipathic polymer having a molecular weight of not less than 5000, are superior to the products of Comparative Examples B1 and B2 in terms of stability over time of retinol acetate serving as a vitamin A fatty acid ester.

TABLE B2

|  | Example | | | | | | |
|---|---|---|---|---|---|---|---|
|  | B4 | B5 | B6 | B7 | B8 | B9 | B10 |
| (Oil phase) | | | | | | | |
| Retinol acetate | 0.2 | 0.2 | 0.2 | 0.2 | 0.2 | 0.2 | 0.2 |
| BHT | 0.05 | 0.05 | 0.05 | 0.05 | 0.05 | 0.05 | 0.05 |
| Pentaerythritol tetra-2-ethyl-hexanoate | — | 5.0 | 10.0 | 15.0 | 20.0 | — | — |
| Squalane | 20.0 | 15.0 | 10.0 | 5.0 | — | — | — |
| Cetyl 2-ethyl-hexanoate | — | — | — | — | — | 20.0 | — |
| Glycerin tri(2-ethylhexanoate) | — | — | — | — | — | — | 20.0 |
| NATROSOL Plus330 | 3.0 | 3.0 | 3.0 | 3.0 | 3.0 | 3.0 | 3.0 |
| (Aqueous phase) | | | | | | | |
| Trisodium edetate | 0.02 | 0.02 | 0.02 | 0.02 | 0.02 | 0.02 | 0.02 |
| Carboxyvinyl-polymer | 0.3 | 0.3 | 0.3 | 0.3 | 0.3 | 0.3 | 0.3 |
| KOH | 0.08 | 0.08 | 0.08 | 0.08 | 0.08 | 0.08 | 0.08 |
| Glycerin | 5.0 | 5.0 | 5.0 | 5.0 | 5.0 | 5.0 | 5.0 |
| Methylparaben | 0.2 | 0.2 | 0.2 | 0.2 | 0.2 | 0.2 | 0.2 |
| Ion-exchange water | B | B | B | B | B | B | B |

TABLE B2-continued

|  | Example | | | | | | |
| --- | --- | --- | --- | --- | --- | --- | --- |
|  | B4 | B5 | B6 | B7 | B8 | B9 | B10 |
| Σ I.O.B. value | 0.0 | 0.104 | 0.197 | 0.279 | 0.353 | 0.128 | 0.353 |
| Percent residue of retinol acetate (%) | 84 | 86 | 90 | 93 | 95 | 87 | 94 |
| Estimation | P | P | P | P | P | P | P |

B: Balance, P: Passed

The products of Examples B4 through B10 shown in Table B2 were studied in terms of correlation between stability of the vitamin A fatty acid ester over time and Σ I.O.B value, in accordance with composition of ingredients in the oil phase.

As is apparent from Table B2, when the Σ I.O.B value is high; i.e., when the oil phase of the composition has high inorganic properties and polarity, the vitamin A fatty acid ester exhibits improved stability over time.

TABLE B3

|  | Example B11 | Comparative Example B3 |
| --- | --- | --- |
| (Oil phase) | | |
| Retinol palmitate | 0.2 | 0.2 |
| BHT | 0.1 | 0.1 |
| Pentaerythritol tetra-2-ethyl-hexanoate | 20.0 | 20.0 |
| Poly (oxyethylene · oxypropylene) methylpolysiloxane copolymer | 5.0 | — |
| POE (20) stearyl ether | — | 5.0 |
| (Aqueous phase) | | |
| Trisodium edetate | 0.02 | 0.02 |
| Carboxyvinylpolymer | 0.3 | 0.3 |

TABLE B3-continued

|  | Example B11 | Comparative Example B3 |
| --- | --- | --- |
| KOH | 0.1 | 0.1 |
| Glycerin | 5.0 | 5.0 |
| Methylparaben | 0.1 | 0.1 |
| Ion-exchange water | Balance | Balance |
| Σ I.O.B. value | 0.353 | 0.353 |
| Percent residue of retinol palmitate (%) | 97 | 75 |
| Estimation | Passed | Not passed |

In the products of Example B11 and Comparative Example B3 shown in Table B3, retinol palmitate was incorporated as a vitamin A fatty acid ester. As is apparent from Table B3, whichever vitamin A fatty acid ester is incorporated, the second emulsion composition or the second external-use composition of the present invention exhibits improved stability of the ester over time.

C. The Third Emulsion Composition of the Present Invention or the Third External-Use Composition of the Present Invention

TABLE C1

|  | Example | | | | | | | | | Comparative Example | | | |
| --- | --- | --- | --- | --- | --- | --- | --- | --- | --- | --- | --- | --- | --- |
|  | C1 | C2 | C3 | C4 | C5 | C6 | C7 | C8 | C9 | C1 | C2 | C3 | C4 |
| (Oil phase) | | | | | | | | | | | | | |
| Retinol acetate | 0.2 | 0.2 | 0.2 | 0.2 | 0.2 | 0.2 | 0.2 | 0.2 | 0.2 | 0.2 | 0.2 | 0.2 | 0.2 |
| BHT | 0.1 | 0.1 | 0.1 | 0.1 | 0.1 | 0.1 | 0.1 | 0.1 | 0.1 | 0.1 | 0.1 | 0.1 | 0.1 |
| Pentaerythritol Tetra-2-ethyl-hexanoate | 20.0 | 20.0 | 20.0 | 10.0 | 10.0 | 8.0 | 16.0 | 3.0 | 5.0 | 20.0 | 20.0 | 20.0 | 20.0 |
| Behenyl alcohol | 1.5 | 2.1 | 3.0 | 7.5 | 7.5 | — | — | 6.0 | — | 1.8 | — | 2.0 | — |
| Stearyl alcohol | — | — | — | — | — | 5.0 | 5.0 | — | 5.0 | — | — | — | — |
| Cetyl alcohol | — | — | — | — | — | — | — | — | — | — | 4.0 | — | 6.0 |
| Myristyl alcohol | — | — | — | — | — | — | — | — | — | — | — | — | 1.5 |
| Ethylparaben | 0.1 | 0.1 | 0.1 | 0.1 | 0.1 | 0.1 | 0.1 | 0.1 | 0.1 | 0.1 | 0.1 | 0.1 | 0.1 |
| Butylparaben | 0.1 | 0.1 | 0.1 | 0.1 | 0.1 | 0.1 | 0.1 | 0.1 | 0.1 | 0.1 | 0.1 | 0.1 | 0.1 |
| (Aqueous phase) | | | | | | | | | | | | | |
| Trisodium edetate | 0.1 | 0.1 | 0.1 | 0.1 | 0.1 | 0.1 | 0.1 | 0.1 | 0.1 | 0.1 | 0.1 | 0.1 | 0.1 |
| Glycerin | 5.0 | 5.0 | 5.0 | 5.0 | 5.0 | 5.0 | 5.0 | 5.0 | 5.0 | 5.0 | 5.0 | 5.0 | 5.0 |
| POE (20) behenyl ether | 3.0 | 3.0 | 3.0 | — | — | — | — | 3.0 | — | 4.0 | — | 10.0 | — |
| POE (20) stearyl ether | — | — | — | 5.0 | 3.0 | 3.0 | 3.0 | — | 3.0 | — | — | — | — |
| POE (15) oleyl ether | — | — | — | — | — | — | — | — | — | — | 10.0 | — | 3.0 |
| Ion-exchange water | B | B | B | B | B | B | B | B | B | B | B | B | B |

TABLE C1-continued

|  | Example | | | | | | | | | Comparative Example | | | |
| --- | --- | --- | --- | --- | --- | --- | --- | --- | --- | --- | --- | --- | --- |
|  | C1 | C2 | C3 | C4 | C5 | C6 | C7 | C8 | C9 | C1 | C2 | C3 | C4 |
| Σ I.O.B. Estimation | 0.344 | 0.340 | 0.337 | 0.299 | 0.299 | 0.325 | 0.335 | 0.269 | 0.316 | 0.343 | 0.346 | 0.342 | 0.345 |
| Percent residue of retinol acetate (%) (50° C., one month) | 83 | 86 | 88 | 81 | 83 | 81 | 85 | 81 | 80 | 72 | 40 | 35 | 73 |

B: Balance

The products of Examples C1 through C3 and Comparative Example C1 shown in Table C1 were compared in terms of the weight ratio of an amphipathic substance to a hydrophilic nonionic surfactant.

As is apparent from Table C1, in the products of Examples C1 through C3, wherein the ratio falls within the allowable range (i.e. not less than 0.5), retinol acetate serving as a vitamin A fatty acid ester is stabilized over time, whereas in the product of Comparative Example C1, wherein the ratio is 0.45, the stability of the ester is poor; i.e., the percent residue is less than 80% (the benchmark value).

The products of Examples C4 and C5 and Comparative Examples C2 and C3 were compared in terms of the amount of the incorporated surfactant.

As is apparent from Table C1, the products of Examples C4 and C5, wherein the amount falls within the allowable range (i.e., not more than 5.0 wt. % with respect to the entirety of the composition), exhibit improved stability of the vitamin A fatty acid ester over time, whereas in the products of Comparative Examples C2 and C3, wherein the amount is outside the range, the stability is decreased drastically.

The products of Examples C6 through C9 were compared in terms of the amount of incorporated oily ingredients.

As is apparent from the Table C1, the products of Examples C6 and C7, wherein the amount falls within the preferred range (i.e. the weight ratio to the total amount of an amphipathic substance and a hydrophilic nonionic surfactant is not less than 1.0), are good in terms of stability of the vitamin A fatty acid ester over time, whereas in the compositions of Examples C8 and C9, wherein the amount is outside the preferred range, the percent residue of the ester is close to the benchmark value (80%).

The product of Comparative Example C4 contains a formulation of an amphipatic substance-hydrophilic nonionic surfactant-water system, in order to obtain a gel transition temperature of less than 50° C.

As is apparent from Table C1, in the product of Comparative Example C4 containing the system having a gel transition temperature of less than 50° C., the percent residue of the vitamin A fatty acid ester is less than the benchmark value (80%).

TABLE C2

|  | Example | | | | |
| --- | --- | --- | --- | --- | --- |
|  | C10 | C11 | C12 | C13 | C14 |
| (Oil phase) | | | | | |
| Retinol acetate | 0.2 | 0.2 | 0.2 | 0.2 | 0.2 |
| BHT | 0.1 | 0.1 | 0.1 | 0.1 | 0.1 |
| Pentaerythritol tetra-2-ethyl-hexanoate | — | 5.0 | 10.0 | 15.0 | 20.0 |
| Squalane | 20.0 | 15.0 | 10.0 | 5.0 | — |
| Behenyl alcohol | 4.0 | 4.0 | 4.0 | 4.0 | 4.0 |
| Ethylparaben | 0.1 | 0.1 | 0.1 | 0.1 | 0.1 |
| Butylparaben | 0.1 | 0.1 | 0.1 | 0.1 | 0.1 |
| (Aqueous phase) | | | | | |
| Trisodium edetate | 0.1 | 0.1 | 0.1 | 0.1 | 0.1 |
| Glycerin | 5.0 | 5.0 | 5.0 | 5.0 | 5.0 |
| POE (20) behenyl ether | 0.5 | 0.5 | 0.5 | 0.5 | 0.5 |
| Ion-exchange water | Balance | Balance | Balance | Balance | Balance |
| Σ I.O.B. Estimation | 0.039 | 0.113 | 0.187 | 0.261 | 0.332 |
| Percent residue of retinol acetate (%) (50° C., one month) | 83 | 87 | 90 | 95 | 97 |

The products of Examples C10 through C14 shown in Table C2 were compared in terms of stability of the vitamin A fatty acid ester in accordance with composition of the ingredients, with the Σ I.O.B. value serving as an index.

As is apparent from Table C2, when the Σ I.O.B value is high; i.e., when the oil phase of the composition has high inorganic properties and polarity, the composition exhibits improved stability of the vitamin A fatty acid ester over time.

TABLE C3

|  | Example | | | Comparative Example | | | |
| --- | --- | --- | --- | --- | --- | --- | --- |
|  | C15 | C16 | C17 | C5 | C6 | C7 | C8 |
| (Oil phase) | | | | | | | |
| Retinol palmitate | 0.2 | 0.2 | 0.2 | 0.2 | 0.2 | 0.2 | 0.2 |

TABLE C3-continued

|  | Example | | | Comparative Example | | | |
| --- | --- | --- | --- | --- | --- | --- | --- |
|  | C15 | C16 | C17 | C5 | C6 | C7 | C8 |
| BHT | 0.1 | 0.1 | 0.1 | 0.1 | 0.1 | 0.1 | 0.1 |
| Pentaerythritol tetra-2-ethyl-hexanoate | 20.0 | — | 10.0 | 20.0 | — | — | — |
| Di(2-ethylhexyl) succinate | — | 10.0 | 5.0 | — | 20.0 | 3.0 | 20.0 |
| Liquid paraffin | — | — | 5.0 | — | — | — | — |
| Stearyl alcohol | 4.0 | 4..0 | 4.0 | 4.0 | 1.8 | 4.0 | 4.0 |
| Ethylparaben | 0.1 | 0.1 | 0.1 | 0.1 | 0.1 | 0.1 | 0.1 |
| Butylparaben | 0.1 | 0.1 | 0.1 | 0.1 | 0.1 | 0.1 | 0.1 |
| (Aqueous phase) | | | | | | | |
| Trisodium edetate | 0.1 | 0.1 | 0.1 | 0.1 | 0.1 | 0.1 | 0.1 |
| Glycerin | 5.0 | 5.0 | 5.0 | 5.0 | 5.0 | 5.0 | 5.0 |
| POE (20) oleyl ether | 2.0 | 1.0 | 2.0 | 10.0 | 4.0 | 2.0 | 2.0 |
| Ion-exchange water | B | B | B | B | B | B | B |
| Σ I.O.B. | 0.340 | 0.305 | 0.262 | 0.340 | 0.347 | 0.310 | 0.340 |
| Estimation | | | | | | | |
| Percent residue of retinol palmitate (%) (50° C., one month) | 92 | 88 | 85 | 45 | 75 | 38 | 33 |

B: Balance

In the products of Examples C15 through C17 and Comparative Examples C5 through C8 shown in Table C3, retinol palmitate was incorporated, in order to verify that the same results as the above-described Examples and Comparative Examples are obtained when a different vitamin A fatty acid ester is incorporated.

As is apparent from Table C3, whichever vitamin A fatty acid ester is incorporated, the third emulsion composition or the third external-use composition of the present invention exhibits improved stability of the ester over time.

Industrial Applicability

As is described above, the present invention provides an emulsion composition which contains a vitamin A fatty acid ester in a stabilized state and which is particularly useful as an external-use composition.

What is claimed is:

1. An oil-in-water emulsion composition comprising:
   at least 0.0001 wt % vitamin A fatty acid ester;
   at least 0.001 wt % of an oil-soluble antioxidant for preventing oxidation of the vitamin A fatty acid ester; and
   a limited amount of a hydrophilic nonionic surfactant for preventing hydrolysis of the vitamin A fatty acid ester,
   wherein the oil phase of the oil-in-water emulsion composition has a Σ I.O.B. value of not less than 0.043.

2. An oil-in-water emulsion composition comprising:
   at least 0.0001 wt. % vitamin A fatty acid ester;
   at least 0.001 wt. % of an oil-soluble antioxidant for preventing oxidation of the vitamin A fatty acid ester; and
   a nonionic amphipathic polymer having a molecular weight of 5,000 or more for preventing hydrolysis of the vitamin A fatty acid ester,
   wherein the oil phase of the oil-in-water emulsion composition has a Σ I.O.B. value of not less than 0.043.

3. The oil-in-water emulsion composition according to claim 1 wherein the ratio by weight of the hydrophilic nonionic surfactant to the oil phase of the oil-in-water emulsion composition is not more than 0.1, and the total amount of all surfactants incorporated into the composition is not more than 1.0 wt. % with respect to the entirety of the composition.

4. The oil-in-water emulsion composition according to claim 1, wherein the hydrophilic nonionic surfactant is at least one hydrophilic nonionic surfactant having a cloud point of 30° C. or more.

5. The oil-in-water emulsion composition according to claim 1, wherein the total amount of oily ingredients contained in the composition is not less then 1.0 wt. % with respect to the entirety of the composition.

6. The oil-in-water emulsion composition according to claim 2, wherein the total amount of oily ingredients contained in the composition is not less than 1.0 wt. % with respect to the entirety of the composition.

7. The oil-in-water emulsion composition according to claim 1, which assumes an essence form.

8. An oil-in-water emulsion composition comprising:
   at least 0.0001 wt. % of vitamin A fatty acid ester;
   at least 0.001 wt. % of an oil-soluble antioxidant for preventing oxidation of the vitamin A fatty acid ester; and
   an amphipathic substance and the hydrophilic nonionic surfactant being incorporated into the composition under the following conditions 1) through 3):
   1) the gel transition temperature in a three-phase system consisting of the amphipathic substance, the hydrophilic nonionic surfactant, and water is 50° C. or higher;
   2) the ratio by weight of the amDhipathic substance to the hydrophilic nonionic surfactant is 0.5 or more; and
   3) the total amount of all surfactants incorporated into the composition is 5.0% by weight or less with respect to the entirety of the composition,
      for preventing hydrolysis of the vitamin A fatty acid ester.

9. The oil-in-water emulsion composition according to claim 8, wherein the weight ratio of the entirety of the oily ingredients contained in the composition to the total amount of the amphipathic substance and the hydrophilic nonionic surfactant is not less than 1.0.

10. The oil-in-water emulsion composition according to claim 8, which assumes a cream form.

11. The oil-in-water emulsion composition according to claim 8, wherein the oil phase of the oil-in-water emulsion composition has a Σ I.O.B. value of not less than 0.043.

12. The oil-in-water emulsion composition according to claim 1, which is a composition for external use.

13. The oil-in-water emulsion composition according to claim 2, which is a composition for external use.

14. The oil-in-water emulsion composition according to claim 8, which is a composition for external use.

15. The oil-in-water emulsion composition according to claim 2, wherein the amount of the nonionic amphipathic polymer having a molecular weight of 5,000 or more is 0.01–10.0 wt. % with respect to the entirety of the composition.

16. The oil-in-water emulsion composition according to claim 2, which assumes an essence form.

* * * * *